US009857243B2

(12) United States Patent
Wilkinson et al.

(10) Patent No.: US 9,857,243 B2
(45) Date of Patent: Jan. 2, 2018

(54) SELF-CORRECTING CHEMICAL SENSOR

(71) Applicant: MATRIX SENSORS, INC., San Diego, CA (US)

(72) Inventors: Paul R. Wilkinson, El Segundo, CA (US); Steven Yamamoto, San Diego, CA (US)

(73) Assignee: Matrix Sensors, Inc., San Diego, CA (US)

( * ) Notice: Subject to any disclaimer, the term of this patent is extended or adjusted under 35 U.S.C. 154(b) by 275 days.

(21) Appl. No.: 14/660,870

(22) Filed: Mar. 17, 2015

(65) Prior Publication Data
US 2017/0023511 A1 Jan. 26, 2017

Related U.S. Application Data

(60) Provisional application No. 61/955,164, filed on Mar. 18, 2014.

(51) Int. Cl.
G01L 1/10 (2006.01)
G01N 27/22 (2006.01)
G01N 33/00 (2006.01)
G01N 27/416 (2006.01)
G01N 29/02 (2006.01)
G01N 29/036 (2006.01)
G01N 29/24 (2006.01)
G01N 29/44 (2006.01)

(52) U.S. Cl.
CPC .............. G01L 1/10 (2013.01); G01N 27/221 (2013.01); G01N 27/4163 (2013.01); G01N 29/022 (2013.01); G01N 29/036 (2013.01); G01N 29/2406 (2013.01); G01N 29/4427 (2013.01); G01N 33/0006 (2013.01); *G01N 2291/0255* (2013.01); *G01N 2291/0256* (2013.01); *G01N 2291/0427* (2013.01); *G01N 2291/106* (2013.01)

(58) Field of Classification Search
CPC ............. G01N 27/221; G01N 27/4163; G01N 33/0006; G01L 1/10
See application file for complete search history.

(56) References Cited

U.S. PATENT DOCUMENTS

| | | | |
|---|---|---|---|
| 6,016,688 A | 1/2000 | Hiss, III et al. | |
| 7,178,378 B2 | 2/2007 | Crawley | |
| 7,305,883 B2 | 12/2007 | Khuri-Yakub | |
| 7,369,004 B2 | 5/2008 | Partridge | |

(Continued)

*Primary Examiner* — Hezron E Williams
*Assistant Examiner* — David Z Huang
(74) *Attorney, Agent, or Firm* — Mark B. Floyd

(57) ABSTRACT

An array of resonant sensors self-corrects measured values for the effects of environmental conditions, such as operating temperature, pressure or humidity. The resonant sensors have varied frequency responses to N environmental parameters and M chemical parameters. Each of the sensors has a different, non-zero frequency response to at least two of the parameters. The device also comprises at least one detector for detecting frequency responses of the resonant sensors. Individual parameter values are determined for each of the N environmental parameters and M chemical parameters according to the detected frequency responses and a system of equations using calibration terms that relate the frequency responses to the individual parameter values.

24 Claims, 8 Drawing Sheets

(56) References Cited

U.S. PATENT DOCUMENTS

| | | |
|---|---|---|
| 7,446,619 B2 | 11/2008 | Partridge |
| 7,446,620 B2 | 11/2008 | Partridge |
| 7,824,098 B2 | 11/2010 | Melamud |
| 7,914,203 B2 | 3/2011 | Mortet |
| 8,256,298 B2 | 9/2012 | Suijlen |
| 8,348,504 B2 | 1/2013 | Gregory |
| 8,424,370 B2 | 4/2013 | Cable |
| 8,427,251 B2 | 4/2013 | Quevy |
| 2007/0235636 A1 | 10/2007 | Blumberg |
| 2010/0107735 A1 | 5/2010 | Pavlovsky |
| 2010/0321191 A1* | 12/2010 | Gong ..................... G01N 22/02 340/584 |
| 2011/0210801 A1 | 9/2011 | Rottenberg |
| 2012/0078541 A1 | 3/2012 | Hesketh |
| 2012/0210794 A1 | 8/2012 | Goehlich |
| 2014/0031263 A1* | 1/2014 | Norling ................... G01N 5/02 506/35 |
| 2014/0032153 A1* | 1/2014 | Mayer ................ G01N 33/0006 702/104 |

* cited by examiner

SELF-CORRECTING CHEMICAL SENSOR

CROSS REFERENCE TO RELATED APPLICATIONS

This application claims the benefit of U.S. provisional patent application 61/955,164 filed on Mar. 18, 2014, which application is hereby incorporated by reference in its entirety.

BACKGROUND

The invention relates to sensor arrays for detecting substances, and in particular to a chemical sensor that self-corrects measured values for the effects of environmental conditions, such as operating temperature, pressure or humidity.

Resonant sensors use target molecules adsorbed in the sensing material to change properties that are reflected in the resonance frequency. A wide variety of cantilever, membrane and piezoelectric resonator-based sensors have been fabricated using MEMS technology. These sensors generally detect agents through the use of polymer films and coatings with selective adsorption for a specific agent or set of agents. Although these sensors provide a certain degree of sensitivity, it is desirable in many applications to have sensors with even higher sensitivities.

A capacitive micromachined ultrasonic transducer (cMUT) is a micromachined device having a substrate and a membrane supported above the substrate by an insulating material. A variable voltage applied between the substrate and membrane drives the membrane to vibrate and emit sound waves at ultrasonic frequencies. Arrays of cMUTs have been used for transmitting and receiving ultrasonic beam patterns in air and water over a frequency range from 10 kHz to 100 MHz. These cMUTs rely on the very large electric field ($E > 10^8$ V/m) in the gap of the capacitor to provide an electromechanical coupling coefficient close to unity.

cMUTs are mostly used for medical imaging. In addition, they have been used to indirectly measure various fluid characteristics, based on processing of ultrasonic signals transmitted and received through the fluid. Due to their resonant character, cMUT devices have the potential to be used as sensors, in a manner similar to MEMS cantilever, membrane, and piezoelectric resonator-based sensors.

U.S. Pat. No. 7,305,883 to Khuri-Yakub discloses such arrays of sensors. Sensor elements include a functionalized membrane supported over a substrate by a support frame. The sensor element is connected to an electrical circuit, which is configured to operate the sensor element at or near an open circuit resonance condition. The mechanical resonance frequency of the functionalized membrane is responsive to binding of an agent to the membrane. The exterior surface of each sensor membrane is chemically functionalized to have an affinity for one or more specific, predetermined chemicals. A detector provides a sensor output responsive to the mechanical resonance frequency of the sensor element.

U.S. Pat. No. 8,424,370 to Cable and Steiert discloses a method for analyzing liquid samples by applying a liquid to a cMUT device having an array of sensors, drying the sensors, and electronically detecting an agent bound to each of the plurality of sensors. An electrical circuit provides a sensor output responsive to a mechanical resonance frequency of the sensor. The exterior surface of sensor membrane is chemically functionalized to have an affinity for one or more specific, predetermined chemicals. The mechanical resonance frequency of the sensor is responsive to the adsorption of a substance of interest to the functionalized membrane, and the mass of the substance that is bound to each of the sensors may be determined.

A resonating member of a sensor, such as a functionalized membrane, may generally detect substances of interest through the use of polymer films and coatings with selective adsorption for specific molecules or sets of target molecules. In practice, nearly every resonating sensor is responsive to other physical or chemical parameters, such as temperature, pressure, humidity, light, other interfering chemical species, etc. In real world operating conditions, the measurements of frequency responses (e.g., changes in resonance frequencies of the sensors) may be significantly affected by environmental conditions such as temperature, pressure and/or interfering gases, thereby masking detection or identification of the true mass of a substance of interest on the sensors. A problem to be solved is how to account for these environmental parameters.

SUMMARY

According to one aspect, a device comprises an array of resonant sensors having varied frequency responses to N environmental parameters and M chemical parameters, where N is an integer greater than or equal to 2, and M is an integer greater than or equal to 1. Each of the sensors has a different, non-zero frequency response to at least two of the parameters (e.g., two of the environmental parameters, two of the chemical parameters, or at least one environmental and one chemical parameter). The device also comprises at least one detector for detecting frequency responses of the resonant sensors. At least one processor is in communication with the detector for receiving signals or data representative of the frequency responses. The processor is programmed to determine individual parameter values for each of the N environmental parameters and M chemical parameters according to the detected frequency responses and a system of equations using calibration terms that relate the detected frequency responses to the individual parameter values. Each of the individual parameter values is calculated using the frequency responses of at least two sensors and the corresponding calibration terms.

According to another aspect, a method comprises exposing a sensor array to a sample. The sensor array comprises a plurality of resonant sensors having varied frequency responses to N environmental parameters and M chemical parameters, where N is an integer greater than or equal to 2, and M is an integer greater than or equal to 1. Each of the sensors has a different, non-zero frequency response to at least two of the parameters. The method also comprises detecting frequency responses of the sensors to the sample. At least one processor is employed to determine individual parameter values for each of the N environmental parameters and M chemical parameters according to the detected frequency responses and a system of equations using calibration terms that relate the detected frequency responses to the individual parameter values. Each of the individual parameter values is calculated using the frequency responses of at least two sensors and the corresponding calibration terms.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. a signal or data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links. According to some embodiments, the present invention provides, inter alia, computer systems comprising hardware (e.g. one or more processors and associated memory) programmed to perform the methods described herein, as well as computer-readable media encoding instructions to perform the methods described herein.

The following description illustrates embodiments of the invention by way of example and not necessarily by way of limitation.

Figure 1:
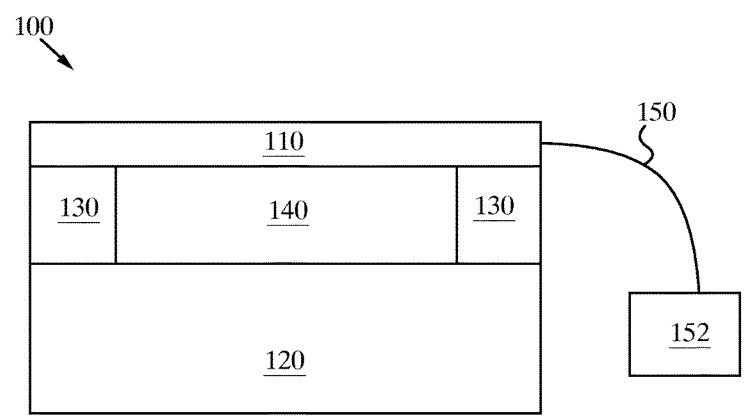
FIG. 1 shows a schematic, cross-sectional view of a sensor according to one embodiment of the invention.

FIG. 1 is a schematic, cross-sectional diagram of a resonator sensor, according to some embodiments of the invention. Resonator sensors include, without limitation, capacitive micromachined ultrasonic transducer (cMUT), cantilever, quartz crystal microbalances, and piezoelectric resonator-based sensors. The resonating sensor typically has a resonating member (e.g., a membrane or cantilever) that oscillates at a frequency. FIG. 1 shows a cMUT sensor 100 that has a membrane 110. The membrane 110 is supported over a substrate 120 by support frame 130. The membrane 110, support frame 130 and substrate 120 define a vacuum gap 140. The sensor 100 is connected to a detector 152 through connector 150.

The detector 152 employs a detection modality to measure frequency responses (e.g., a change in frequency of the resonating member of the sensor 100) due to environmental parameters and chemical parameters. Environmental parameters include, but are not limited to temperature, pressure, humidity, light, dust and/or interfering gases. Chemical parameters include but are not limited to the quantity or concentration of a target analyte and/or the mass of one or more analytes (e.g., target molecules) that are adsorbed or bound to the sensors. In preferred embodiments, the detector 152 detects a resonance frequency of the functionalized membrane 110, which frequency may change when the sensor 100 is exposed to a sample during operation due to the environmental and/or chemical parameters. Suitable detectors include, but are not limited to, an optical detector, a mechanical stress detector, a magnetic detector, and a capacitance detector. In some embodiments, an oscillator circuit is used in conjunction with a frequency counter to detect the frequency responses of the membrane 110. In other embodiments, a sweep system is employed, where electronics sweep a wide range of frequencies to record an entire resonance curve.

In some embodiments, the membrane 110 is driven electrically or thermally (by applied heat or by thermal noise), and an optical detector is used to detect deflection or resonant frequency shifts of the membrane 110. Interferometric optical detection techniques are described in U.S. Pat. No. 6,567,572, by Degertekin et al., which is incorporated herein by reference. In other embodiments, the membrane 110 has thin piezoelectric or magnetic films that provide coupling. The membranes 110 may be addressed by capacitor action (cMUTs), by a piezoelectric thin film (pMUTs), or by a magnetic film on the surface (mMUTs). Alternatively, a frequency response may be detected directly through a change in capacitance, or magnetic field, or piezoelectric signal, or change in resistance through the piezoresistive effect. Preferably, the membrane 110 operates at a mechanical resonance frequency of at least about 1 MHz, more preferably between about 1 MHz and about 100 MHz.

Figure 2:
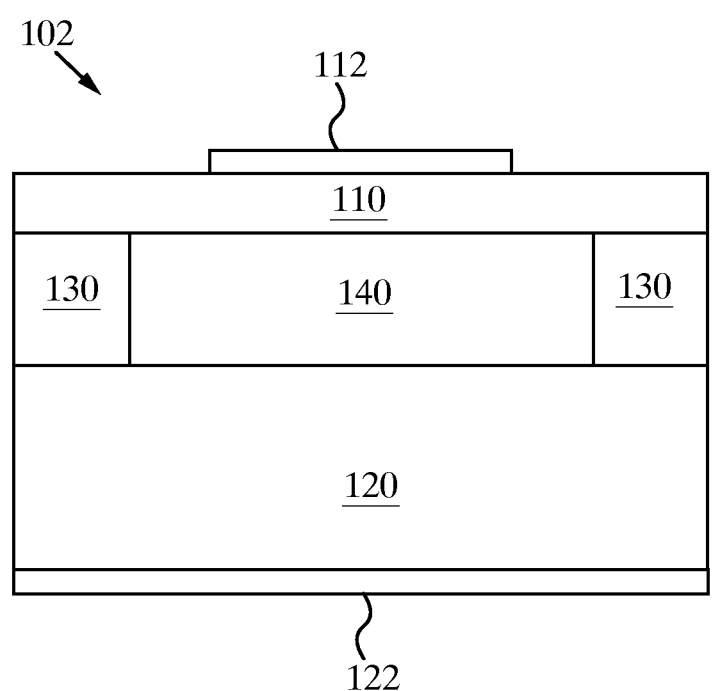
FIG. 2 shows a schematic cross-sectional view, of a sensor according to another embodiment of the invention.

FIG. 2 shows a cMUT sensor 102 having a membrane 110 that includes a first electrode 112. The substrate 120 contains a second electrode 122. Functionalized membrane 110 and substrate 120 are preferably thin membranes that are essentially parallel plate capacitors with a gap between the plates. In a preferred aspect of this embodiment, the conductive silicon wafer on which the functionalized membrane is fabricated, i.e. substrate 120, makes up one plate of the capacitor. A metal electrode 112 on top of the functionalized membrane 110 is the other plate of the capacitor. The membrane 110, which is supported by insulating support frame 130, is typically made of an insulating material, most commonly silicon, and is coated with the electrode 112. A low temperature oxide passivation layer may cover electrode 112 and functionalized membrane 110.

Figure 3:
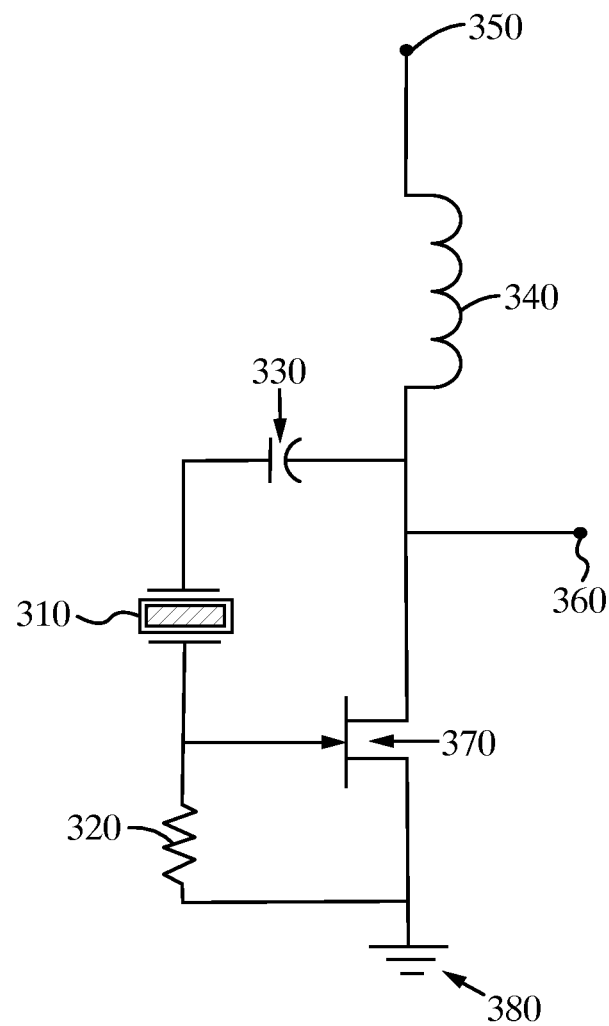
FIG. 3 shows an example of an electrical circuit for a sensor according to some embodiments of the invention.

FIG. 3 shows one embodiment of a circuit that is suitable for use with a resonant sensor. The circuit is one variation of an oscillator. The circuit includes a resonant sensor 310, resistor 320, capacitor 330, inductor 340, DC voltage source 350, sensor output 360, transistor 370, and connection to ground 380. Many other circuits are available to establish a resonant circuit using the sensor's resonant electrical input impedance (e.g., a Colpitts oscillator, Pierce oscillator, etc.). The output of these circuits is an approximately sinusoidal signal whose frequency is the measurable quantity of interest.

In some embodiments, the sensor is placed in the feedback loop of an amplifier and the gain of the amplifier is adjusted such that the circuit oscillates. The frequency of the oscillator is tuned by adjusting the DC bias that is applied to the sensor element. By controlling this DC bias the resonance or oscillation frequency is placed near the open circuit resonant frequency of the sensor. This may reduce the noise in the oscillator circuit, and hence increase the sensitivity of the sensor. When analyte adsorbs or binds to the receptor material on a resonating member of the sensor (e.g., the membrane 110 or a cantilever), its open circuit resonance frequency shifts, and this imparts a frequency shift in the oscillator circuit. By measuring the resonance frequency of the oscillator, one can estimate how much mass has deposited on the membrane 110.

Figure 4:
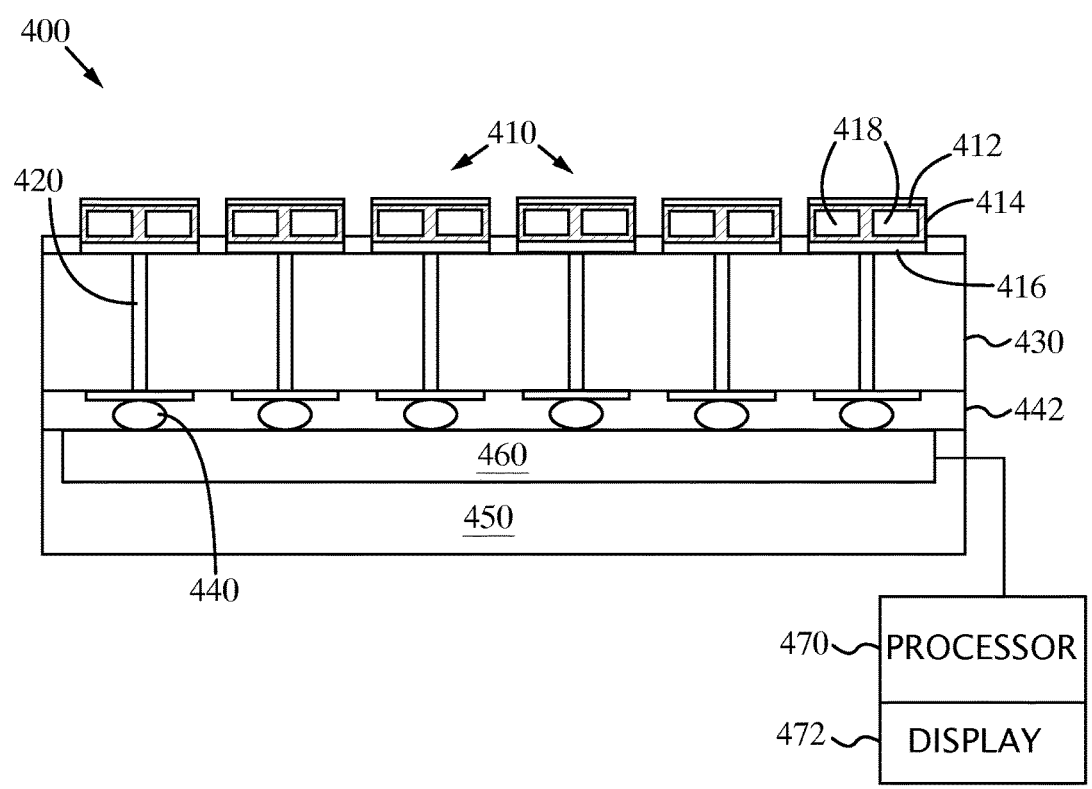
FIG. 4 shows a schematic, cross-sectional view of an array of sensors according to some embodiments of the invention.

FIG. 4 is a schematic cross-sectional view of a sensor device 400 having an array of sensors 410 according to another embodiment of the invention. In this example, each sensor 410 contains two sensor elements, each of which has a membrane 412, support frame 414, substrate 416 and vacuum gap 418. The exterior surface of some of the membranes 412 may be chemically functionalized with a receptor material to bind or adsorb one or more target molecules. The sensors 410 are designed for varied sensitivity to environmental parameters and/or mass loading by substances adsorbed or bound to the membranes 412. The sensors 410 match into the electronic circuitry (e.g., an oscillator) that is used to detect frequency shifts in the membranes 412 due to the environmental parameters (e.g., temperature, pressure, humidity or light) and/or analytes adsorbed or bound to the surface of the membranes 412 when they are present in a sample to which the sensor is exposed. Consequently, the operational characteristics (e.g., impedance or resonance frequency) of the sensor will be altered, and this frequency response is detected.

The presence or amount of substance(s) in a sample is measured by detecting the alteration of the operating characteristics of the resonating member (e.g., a membrane or cantilever). For example, an alteration in sensor characteristics can be detected by measuring the impedance of the sensor, or by measuring the change in the resonant frequency of the functionalized membrane 412. Interconnects 420 through wafer 430 provide electrical contacts from the sensors 410 to a wafer 450 with electronics layer 460. The interconnects 420 are separated from the electronics 460 by an underfill 442 and solder balls 440. (While solder bumps are shown in this figure, contacts may be made between wafer 430 and wafer 450 by any means known in the art, e.g. with an anisotropic conducting film).

The electronics layer 460 contains appropriate circuitry to drive and detect operational characteristics of the sensors 410, such as resonance frequencies of each membrane 412. Additional signal processing electronics or at least one processor 470 may be attached to the sensor electronics to further process the signals or data and to provide an indication of the presence or amount of analyte(s). For example, the presence or amount of analytes may be shown via the display 472 in communication (wirelessly or with wires) with the processor 470. The processor 470 receives data representative of the resonance frequencies (e.g., frequency output signals from the sensors 410) to determine the presence or amount of analyte(s). The processor 470 may be a microprocessor included with the device 400. Alternatively, processing functions may be performed in a separate processor or external computer in communication with the electronics layer 460. The external processor or computer receives data representative of the measured resonance frequencies and determines the presence or amount of analyte(s). Alternatively, multiple processors may be provided, e.g., providing one or more processors in the device 400 that communicate (wirelessly or with wires) with one or more external processors or computers.

Some processing of data can be done near the sensor. For instance, time averaging or multiplexing or digitization can be all processed in the vicinity of the sensor before being transmitted to a computer or a circuit board with a multiprocessor. Specific algorithms can be loaded in memory to perform the same functions one would in a digital computer and then drive displays where colored outputs can be used to indicate level of detection or hazard. As in many sensors deployed today, such as RF tags and implanted medical devices, it is possible to use RF antennas to couple and provide power to the sensor. Once a sensor is powered, it senses its function, and then the output of the sensor is re-radiated to a receiving antenna. In this fashion, the sensor device 400 can be passive and remotely addressed.

In some embodiments, a CMOS provides the circuitry to detect the frequency responses of the membranes 412 either through an impedance change, by direct measurement, resonance frequency measurement, or any of various other means. The outputs of various sensors can be multiplexed, then a frequency counter can measure the frequencies. These outputs can then be digitized and stored and processed in a processor. The processor then can display the variation of the resonant frequency versus time and provide results of analysis of sensed species based, for example, on previously loaded models of sensitivity of multiple sensors to various chemicals.

The material properties and dimensions of the membranes 412 contribute to their resonant frequencies. In some embodiments, a DC bias is applied to the functionalized membranes 412 to maintain a very high electric field in the vacuum gaps 418. For instance, a silicon membrane 12 µm in diameter and 0.4 µm thick may resonate at a frequency of 42 MHz. In some embodiments, each sensor is used as the resonant tank of an oscillator circuit, where the resonant frequency shift indicates the amount of mass loading on the membranes 412. The sensitivity of such a resonator is defined as the ratio of the frequency shift over the frequency: $\Delta f/f = -\Delta m/2m$, where $\Delta m$ is the change in mass (i.e., mass of the species that adsorbs or binds to the sensor) over the total mass of the membrane.

In some embodiments, a resonance frequency response of the fundamental mode is replaced or supplemented by measuring a series of higher harmonics of the membrane. The viscoelastic properties of the sensing layer (e.g., receptor material on the resonating member) are influenced by absorption/adsorption. These properties may be extracted through measuring the frequency dependence of the damping and the amplitude of higher order modes, and these measurements provide chemical information in addition to the resonance frequency. For instance, different mass loadings, polymer swelling and changes in the young modulus are detected through the amplitude and Q-factor. Off-resonance response may also provide information on viscoelasticity through the slope of the mechanical response. In some instances, the resonating member of a sensor can be engineered to enhance the response at some harmonics.

Sensor arrays may be configured as one-dimensional arrays of sensors or two-dimensional arrays of sensors. An advantage of a two-dimensional array is that an entire wafer may be populated with a larger number of resonant sensors. A one-dimensional array provides more surface space, which may be used to integrate electronics side-by-side with the sensors. In some embodiments, a two-dimensional sensor array has electronics flip-chip bonded or fabricated under the sensor array. A sensor array with thousands of resonating members may be useful in some embodiments for establishing electrical impedance of the sensor, or for reducing the number of false alarms through redundancy.

Figure 5:
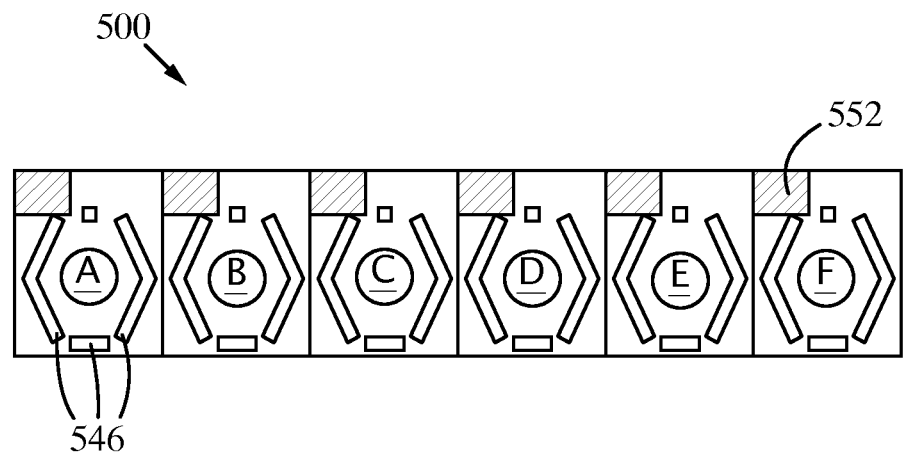
FIG. 5 shows a schematic, plan view of an array of sensors according to some embodiments of the invention.

FIG. 5 shows a sensor array 500 having one row of six resonator sensors A-F. To mechanically isolate each of the sensors or reduce crosstalk between the sensors, vertical trenches 546 may be added between each of the sensors. The trenches 546 may be formed by any known etching process. Each of the sensors may also include wire bond pad areas 552 for electrical connections. Each of the sensors A-F has a respective resonating member (e.g., a membrane or cantilever). One or more of the resonating members may be coated with a receptor material that adsorbs, absorbs or binds a target substance in a sample.

In some embodiments, the receptor material is a porous crystalline material such as a metal-organic framework (MOF), porous coordination polymer, or porous coordination framework. Preferred MOF subclasses include Zeolitic imidazolate framework (ZIF), IRMOF, and Multivariate MOF (MTV-MOF) made using a mix of organic linkers having the same geometry but varied chemical functionality. Suitable porous receptor materials also include a covalent organic framework (COF) in which the framework includes covalent chemical bonds rather than metal coordination bonds, and Zeolite which is a class of inorganic porous crystalline materials. In rare embodiments, the porous receptor materials comprise non-crystalline porous materials such as Metal-organic Polyhedron having discreet porous cages, Porous metal-organic polymer, Metal-organic gel, or Porous Carbon (also known as activated carbon).

Metal-organic frameworks (MOFs) are an expanding class of porous crystalline materials that are built up from nodes of metal ions connected by organic linkers. These materials can typically be engineered to have pore apertures with a width or diameter in a range of less than 1 Angstrom to about 30 Angstroms (Yaghi, et. al., Nature 423, 705-714, Jun. 12, 2003). A class of exotic MOFs ("MOF-74") with pore aperture diameters of 98 Angstroms have also been demonstrated (Deng, et. al., Science 336, 1018, 2012). MOFs with varying pore sizes can selectively adsorb molecules based on the size of the molecules. For example, engineered MOFs with pore sizes designed for carbon dioxide ($CO_2$) adsorption can separate gases in industrial processes (Du, et. al., J. Am. Chem. Soc., 2013, 135 (2), pp 562-565). MOFs can also be used as receptor layers with a Quartz Crystal Microbalance (QCM) to act as a chemical sensor in controlled environments. When one or more types of MOFs is used as a receptor material on a resonant sensor, the surface of the resonating member may be prepared for MOF growth with a self-assembled monolayer (SAM) or by deposition of either an oxide or metal surface. The MOF coating on the resonating member preferably has a thickness in the range of 1 to 1000 nm.

In some embodiments, resonant sensors are functionalized with polymers having different properties so that the sensor array can sensitively detect and differentiate chemical compounds, and even complex mixtures. One may select and test an optimum set of polymers as receptor materials to generate a robust signature pattern for an analyte. Polymer receptor materials respond to gas-phase analytes in seconds to tens of minutes. The selection of polymers is preferably optimized to fit the mechanical properties of the resonating members of the sensors (elasticity, density, thickness, etc.), so that detection time is minimized and sensitivity is maximized.

The surfaces of the resonating members of the sensors A-F may be functionalized in a manner that improves the receptor material's stability, control analyte adsorption kinetics, and ease application of the receptor material. Sensors may be functionalized (e.g., coated) with receptor materials in various ways including the use of electrospray, spin-coating, ink jet techniques, spotter techniques, microfluidics, self-assembly, shadow masking coupled with the above, or spraying in vacuum through movable mask arrays. Functionalization of the resonating members may be performed by first coating the exterior surface of the resonating members with a metal such as gold that aids adhesion of a receptor material to the surface. The receptor material may be deposited on the surface using various techniques, such as drop ejection, that enable multiple functionalizing liquids to be deposited on the sensor surface, and also reduce or eliminate cross-contamination between adjacent functionalized cells of an array. In some embodiments, neutral polymer gels may be used as carriers for receptor materials. Using this method, a variety of compounds that do not form stable films themselves can be applied through drop or spin coating on a neutral substrate such as silicon dioxide.

In order to control the location, applications, volume, and quantity of liquids deposited on the surface, one may use ink jet technology with functionalizing receptor materials instead of inks. It is sometimes preferable to use non-thermal deposition technology, if thermal ink jets would harm sensitive fluids. A drop ejector, for example, may be used to deposit the polymer over a sensor. The drop ejector is preferably used to deposit enough drops to cover a sensor. Different ejectors are used for different receptor materials so that adjacent sensors and membranes can be functionalized differently. One deposition technique is to use ultrasound based ejectors where a focused beam evolves a drop from a free surface.

Sensors may be coated or functionalized with various types of receptor materials for specific applications. These materials include, for example, porous receptor materials as listed above, polymers (co-polymers, bio-polymers), sol gels, and DNA, RNA, proteins, cells, bacteria, carbon nanotube arrays, catalysts including metals to enzymes, nanoclusters, organic and inorganic materials including: supramolecules, metal-organic complexes, or dendritic materials.

In some embodiments, each of the six sensors A-F has a different receptor material disposed on its resonating member (e.g., a membrane or cantilever). In one example, the receptor material on the first sensor A comprises polyethylenimine, the receptor material on the second sensor B comprises carboxymethyl cellulose, the receptor material on the third sensor C comprises polyethylene glycol, the receptor material on the fourth sensor D comprises poly(styrenesulfonate), the receptor material on the fifth sensor E comprises polyvinylpyrrolidone, and the receptor material on the sixth sensor F comprises poly(methyl methacrylate).

Figure 6A:
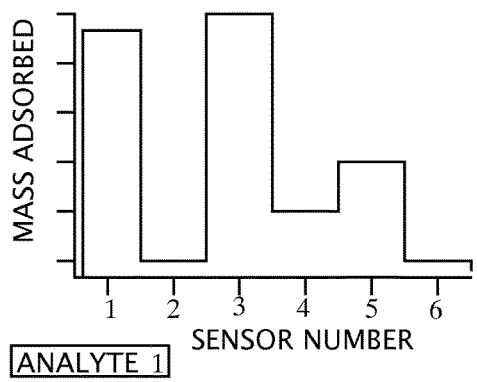
FIGS. 6A-6D are graphs showing patterns of masses adsorbed on sensors according to some embodiments of the invention.
Figure 6B:
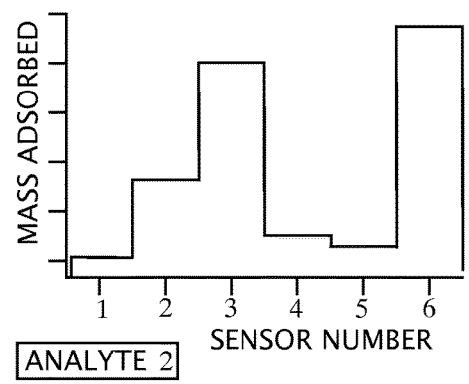
Figure 6C:
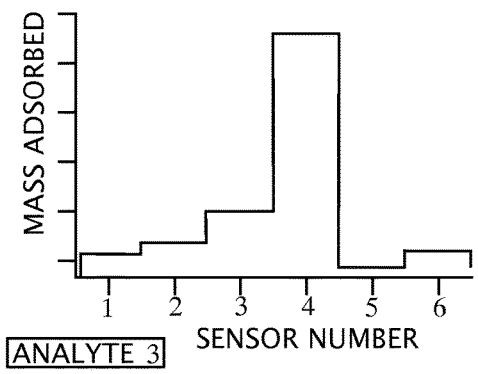
Figure 6D:
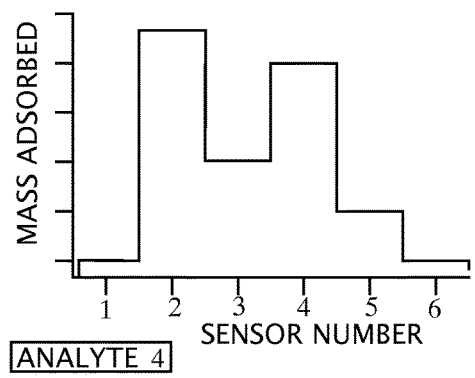

FIGS. 6A-6D are graphs showing patterns of masses adsorbed on functionalized sensors A-F for four target analytes. In this example, the analytes are volatile organic compounds (VOCs) that adsorb or bind in different mass patterns on the six analyte sensors having different receptor materials disposed thereon. FIG. 6A shows a response pattern of masses of a first analyte, acetaldehyde. FIG. 6B shows a response pattern of a second analyte, benzene. FIG. 6C shows a response pattern of a third analyte, formaldehyde. FIG. 6D shows a response pattern of a fourth analyte, naphthalene.

At least one processor may be employed to determine the presence or amount of the analytes from the detected frequency responses. The processor receives signals or data representative of the frequency responses (e.g., changes in resonance frequencies of the functionalized sensors due to mass loading of substances on the sensors). The processor deconvolves or de-convolutes the data using coefficients. This step can be performed with a set of equations, or more generally by a matrix. In a simple form, let A be the signal amplitude of sensor 1 indicating the sensor response, and X the quantity of unknown target substance adsorbed on the sensor 1. We can describe the dependence of amplitude A and unknown quantity X by a linear relationship and a coefficient $a_x$ so that $A=a_x X$. If there is more than one substance on sensor 1, such as substances X and Y, then $A=a_x X+a_y Y$. If we now let B be the signal amplitude of the second sensor 2 with a different receptor material and affinities $b_x$ and $b_y$, and assume that the second sensor is exposed to the same quantities X and Y of substances (since the sensors are proximate), then we can measure a different value B with the second sensor and solve two equations with two variables:

$$A=a_x X+a_y Y \quad (1)$$

$$B=b_x X+b_y Y \quad (2)$$

More generally, if we know the matrix of coefficients $a_{ij}$, then we can determine the masses of multiple substances $X_j$ if we have measured the amplitudes of I sensors $A_i$ using the vector product (equation 3):

$$A_i = a_{ij} X_j \quad (3)$$

An array of sensors may be calibrated to determine the values of the matrix $a_{ij}$, with known substances of interest $X_j$. In some embodiments, the processor determines respective patterns of masses on the sensors for each substance of interest. The sensor response data may be used with calibration curves to quantify the amount or concentration of one or more analytes (e.g., the ppm concentration of a specific gas), which analyte values may be recorded in memory and/or displayed.

Most measurements of airborne substances are affected by environmental parameters (e.g., temperature pressure, humidity, light, interfering gases, etc.). These environmental parameters can have effects on the frequency responses of the analyte sensors. It is useful to have calibration sensors whose frequency responses may be used to correct the frequency responses from the analyte sensors for the effects of various environmental parameters, to determine an analyte value (e.g., the concentration of a gas) that is substantially independent of environmental variations. We can take advantage of an array of resonant sensors on a single device to compensate the chemical analyte sensors for environmental parameters. The calibration sensors are engineered to have different frequency responses to variations in the environmental parameters.

Resonant sensors may be engineered to have different frequency responses to variations in the environmental or chemical parameters by making structural and/or coating modifications to the resonating members. In addition, structural and coating modifications to the resonating members can usually be combined to create various hybrids. Table 1 describes examples of types of sensors, where the terms "Low, Medium, High" refer to the sensor's sensitivity (e.g., frequency response) to that parameter.

TABLE 1

| | Sensor Description | Type | Temp | Pressure | Light | Humidity | Chemical sensitivity |
|---|---|---|---|---|---|---|---|
| 1 | Thin resonating member (e.g., 100 nm), Teflon-coated | Structure | Medium | High | Medium | Low | Low |
| 2 | Thick resonating member (e.g. 1,000 nm), Teflon-coated | Structure | Medium | Low | Medium | Low | Low |
| 3 | Resonating member with small hole, Teflon-coated | Structure | Medium | Low | Medium | Low | Low |
| 4 | silver (mirror) coated resonating member | Coating | Medium | Medium | Low | Medium | Low |
| 5 | Resonating member with hydrophobic coating (e.g., Teflon) | Coating | Medium | Medium | Medium | Low | Low |
| 6 | Resonating member with hydrophilic coating (e.g., polyvinyl alcohol) | Coating | Medium | Medium | Medium | High | Low |
| 7 | Resonating member with metallic or bi-metallic coating with different coefficients of thermal expansion | Coating | High | Medium | Low | Medium | Low |
| 8 | Resonating member coated with receptor material (e.g. MOF, polymer, etc.) | Coating | Low To High | High | Medium | Low To High | High |

Figure 7A:
FIGS. 7A-7B show schematic side views of resonating members having different thicknesses according to some embodiments of the invention.
Figure 7B:

FIGS. 7A-7B show schematic side views of resonating members 702, 704 (e.g., membranes) having different thicknesses, as described in the first two rows of Table 1. In some embodiments, the resonating member of at least one of the sensors in the array has a thickness that is at least twice the thickness of the resonating member of another one of the sensors in the array. In other embodiments, the ratio of the thicknesses of the resonating members is at least 5:1 or 10:1. For example, the membrane 702 of sensor 1 may have a thickness of 100 nm, while the membrane 704 of sensor 2 has a thickness of 1000 nm. The thinner resonating member has a greater sensitivity (e.g., greater change in resonance frequency) to pressure variation.

Figure 8:
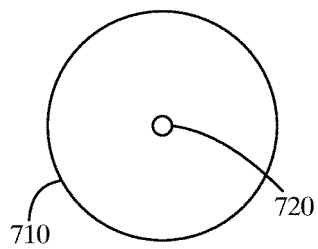
FIG. 8 shows a schematic, plan view of a resonating member with a hole or perforation according to some embodiments of the invention.

FIG. 8 shows a schematic, plan view of a membrane 710 with a roughened surface, perforation or hole 720, as described in row 3 of Table 1. This structural modification to at least one of the sensors in an array is useful for determining pressure. The pressure can be determined from the different frequency responses of at least two sensors with substantially the same membrane thickness, but the sensor with the hole 720 in the membrane 710 is less sensitive (lower frequency response) to pressure than the sensor without a hole.

Figure 9:
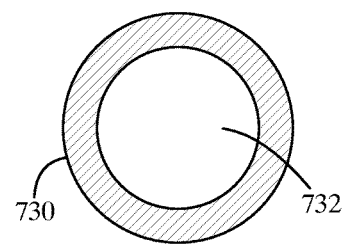
FIG. 9 shows a schematic, plan view of a resonating member having a coating that reflects light according to some embodiments of the invention.

FIG. 9 shows a schematic, plan view of a resonating member 730 having a reflective coating 732 that reflects light, as described in row 4 of Table 1. For example, silver, gold or anodized aluminum may be deposited on a membrane to provide a reflective surface. This coating modification to at least one of the sensors in an array is useful for determining the effects of ambient light. The light effects can be determined from the different frequency responses of at least two sensors in the array, one of the sensors having a reflective coating and the other sensor having either a non-reflective coating or no coating. The resonating member 730 having a reflective coating 732 is less sensitive (lower frequency response) to light than the non-reflective sensor.

Figure 10A:
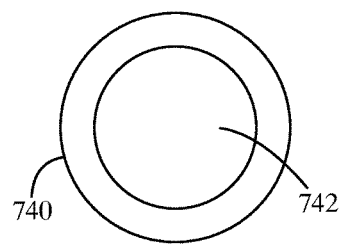
FIGS. 10A-10B show schematic plan views of resonating members having hydrophobic and hydrophilic coatings according to some embodiments of the invention.
Figure 10B:
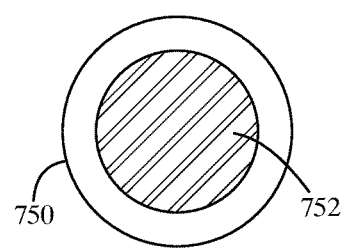

FIGS. 10A-10B show schematic plan views of resonating members 740, 750 having hydrophobic and hydrophilic coatings, respectively, as described in rows 5-6 of Table 1. The resonating member 740 of at least one of the sensors in the array has a hydrophobic coating 742 (e.g., poly methyl methacrylate or polystyrene) relative to a hydrophilic coating 752 (e.g., poly vinyl alcohol) on the resonating member 750 of another one of the sensors in the array. Due to the different affinities to water of the two coating materials on the resonating members 740 and 750, the sensor that is coated with the hydrophilic receptor material shows a strong frequency response to adsorbing or binding water molecules, whereas the sensor that is coated with a hydrophobic receptor material shows little or no response to water. This coating modification to at least one of the sensors in an array relative to another sensor is useful for determining the effects of humidity on frequency response.

Figure 11:
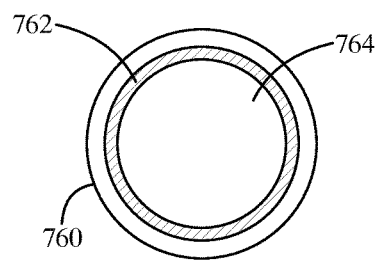
FIG. 11 shows a schematic, plan view of a resonating member with a metallic coating according to some embodiments of the invention.

FIG. 11 shows a schematic, plan view of a resonating member 760 with a single-metallic or bi-metallic coating, as described in row 7 of Table 1. In embodiments where the resonating member 760 is a CMUT membrane, the membrane is typically composed of silicon, or sometimes silicon nitride. These materials (e.g., silicon or silicon nitride) have fairly small thermal expansion coefficients. In some embodiments, a single metal layer (having a high thermal expansion coefficient) is added to the surface of the silicon or silicon nitride, so that the resonating member 760 is thus composed of at least two materials (e.g., silicon and gold) having different coefficients of thermal expansion, in order to create differential thermal strain. The resonating member 760 deflects in response to the thermal strain, resulting in a frequency shift.

A layer of metal (e.g., gold or aluminum) may be coated on the resonating member 760. Preferably the metal layer comprises about 20% of the resulting thickness of the resonating member, with silicon or silicon nitride comprising the other 80% of the thickness. Instead of coating the whole resonating member 760 (e.g., a membrane), in some embodiments, the surface of the resonating member 760 is patterned with metal. In one embodiment, two of the sensors in an array are produced with two different thermal sensitivities of opposite sign by patterning one of the membranes with metal (e.g., gold) such that r/rm>0.52, and by patterning the other membrane with metal such that r/rm<0.52 (where r is the radial coordinate of the metal pattern, and where rm is the total radius of the membrane).

In other embodiments, the resonating member 760 has a bi-metallic coating comprising a first layer of metal 762 (e.g., steel) and a second layer of metal 764 (e.g., copper) deposited on top of the first layer. The two metals 760, 762 have two different coefficients of thermal expansion. These embodiments that include either a single-metallic or bi-metallic coating on at least one of the sensors in an array are useful for determining the effects of temperature. As the temperature changes, the difference in thermal expansion between different materials causes the resonating member 760 to bulge, which action induces a frequency shift. The temperature can be determined from the frequency response of the resonating member 760, or from the different frequency responses of at least two sensors in the array, in which one of the sensors has a resonant member that is composed of at least two materials having different coefficients of thermal expansion so that it is more sensitive to temperature than the other sensor.

In Table 1, the sensors with structural modifications are combined with a Teflon coating to reduce their sensitivity to humidity. However, a structural modification may be combined with any coating as a method to engineer a desired sensitivity to environmental parameters. In addition, the thickness of the coating may be varied to engineer a desired sensitivity to environmental parameters. When polymers are used as receptor materials, the thickness of a coating of a polymer film on a sensor can vary in a practical thickness range of about 10 nm to 500 nm. In some embodiments, the amount of receptor material used to functionalize each sensor may be varied. For example, the number of droplets of receptor material placed on each sensor can be varied from one sensor to the next, thereby varying the thickness of the deposited receptor material. This variation in the amount or thickness of receptor material on each sensor establishes one more pathway to provide different frequency responses to environmental or chemical parameters. In general, the sensors with thicker coatings are more sensitive to humidity.

Referring again to FIG. 5, a first example of the use of calibration sensors will now be given, using the sensor array 500. In this example, the sensors A-C are three calibration sensors that are sensitive to changes in temperature, pressure and humidity. The sensor A is a calibration sensor having a membrane with a perforation or hole, rendering it less sensitive to pressure than the sensors without a hole. The sensor B has a membrane with a hydrophilic coating (e.g., polyvinyl alcohol) so that it is more responsive to humidity than the sensors with a more hydrophobic coating. The sensor C has a membrane with a bi-metallic coating with two different coefficients of thermal expansion (e.g., steel and copper), so that the sensor is more sensitive to temperature than the sensors without a bi-metallic coating. The sensors D-F are three analyte sensors coated with appropriate receptor materials for adsorbing, absorbing or binding target molecules.

An idealized, but nearly impossible-to-realize, sensor array is one where the frequency of the $i^{th}$ channel, $f_i$, responds to only one environmental or chemical parameter. This ideal case is expressed in equation (4):

$$\begin{pmatrix} P_1 \\ P_2 \\ P_n \\ C_1 \\ C_2 \\ C_m \end{pmatrix} = \begin{pmatrix} T_{1,1} & 0 & 0 & 0 & 0 & 0 \\ 0 & T_{2,2} & 0 & 0 & 0 & 0 \\ 0 & 0 & T_{3,3} & 0 & 0 & 0 \\ 0 & 0 & 0 & T_{4,4} & 0 & 0 \\ 0 & 0 & 0 & 0 & T_{5,5} & 0 \\ 0 & 0 & 0 & 0 & 0 & T_{n+m,n+m} \end{pmatrix} \times \begin{pmatrix} f_1 \\ f_2 \\ f_3 \\ f_4 \\ f_5 \\ f_{n+m} \end{pmatrix} \quad (4)$$

Here, there are n environmental parameters, P, and m chemical parameters, C, that are each transduced by a respective one of n+m frequency responses of the sensors, f, via a calibration term, T. In this idealized case, each sensor has a linear frequency response to one, and only one, environmental or chemical parameter. An individual parameter value is calculated for each of the n environmental parameters, P, and m chemical parameters, C, from the frequency response of just one sensor and one corresponding calibration term.

In practice, nearly every resonant sensor is responsive to more than one environmental and/or chemical parameter, such as temperature, pressure, humidity, light, multiple target analytes, other interfering chemical species, etc. The set of sensors A-F in the array 500 may be mutually correcting or self-calibrating. The number of sensors is preferably greater than or equal to the number of environmental plus chemical parameters of interest. Calibration of the sensor array 500 preferably includes populating both the diagonal and off-diagonal elements of a calibration matrix, as shown in equation (5).

$$\begin{pmatrix} P_1 \\ P_2 \\ P_n \\ C_1 \\ C_2 \\ C_m \end{pmatrix} = \begin{pmatrix} T_{1,1} & T_{1,2} & T_{1,3} & T_{1,4} & T_{1,5} & T_{1,n+m} \\ T_{2,1} & T_{2,2} & T_{2,3} & T_{2,4} & T_{2,5} & T_{2,n+m} \\ T_{3,1} & T_{3,2} & T_{3,3} & T_{3,4} & T_{3,5} & T_{3,n+m} \\ T_{4,1} & T_{4,2} & T_{4,3} & T_{4,4} & T_{4,5} & T_{4,n+m} \\ T_{5,1} & T_{5,2} & T_{5,3} & T_{5,4} & T_{5,5} & T_{5,n+m} \\ T_{n+m,1} & T_{n+m,2} & T_{n+m,3} & T_{n+m,4} & T_{n+m,5} & T_{n+m,n+m} \end{pmatrix} \times \begin{pmatrix} f_1 \\ f_2 \\ f_3 \\ f_4 \\ f_5 \\ f_{n+m} \end{pmatrix} \quad (5)$$

Here, there are n environmental parameters, P, and m chemical parameters, C, that are each transduced by a plurality of n+m sensor signals, f, via a plurality of n+m calibration terms, T. An individual parameter value is calculated for each of the n environmental parameters, P, and m chemical parameters, C, from the frequency responses of n+m sensors and a plurality of calibration terms that relate the detected frequency responses to the individual parameter value. In this example, with n+m=6 total environmental plus chemical parameters of interest, an individual parameter value is calculated for the first environmental parameter $P_1$ (pressure) from matrix multiplication in equation (5) as:

$$P_1 = (T_{1,1})^*(f_1) + (T_{1,2})^*(f_2) + (T_{1,3})^*(f_3) + (T_{1,4})^*(f_4) + (T_{1,5})^*(f_5) + (T_{1,6})^*(f_6) \quad (6)$$

Similarly, individual parameter values may be calculated for the other five environmental plus chemical parameters of interest from matrix multiplication in equation (5) as:

$$P_2 = (T_{2,1})^*(f_1) + (T_{2,2})^*(f_2) + (T_{2,3})^*(f_3) + (T_{2,4})^*(f_4) + (T_{2,5})^*(f_5) + (T_{2,6})^*(f_6) \quad (7);$$

$$P_3 = (T_{3,1})^*(f_1) + (T_{3,2})^*(f_2) + (T_{3,3})^*(f_3) + (T_{3,4})^*(f_4) + (T_{3,5})^*(f_5) + (T_{3,6})^*(f_6) \quad (8);$$

$$C_1 = (T_{4,1})^*(f_1) + (T_{4,2})^*(f_2) + (T_{4,3})^*(f_3) + (T_{4,4})^*(f_4) + (T_{4,5})^*(f_5) + (T_{4,6})^*(f_6) \quad (9);$$

$$C_2 = (T_{5,1})^*(f_1) + (T_{5,2})^*(f_2) + (T_{5,3})^*(f_3) + (T_{5,4})^*(f_4) + (T_{5,5})^*(f_5) + (T_{5,6})^*(f_6) \quad (10);$$

$$C_3 = (T_{6,1})^*(f_1) + (T_{6,2})^*(f_2) + (T_{6,3})^*(f_3) + (T_{6,4})^*(f_4) + (T_{6,5})^*(f_5) + (T_{6,6})^*(f_6) \quad (11).$$

In some embodiments, the calibration terms are coefficients (e.g., constants), reflecting a linear frequency response of the sensors to the environmental and chemical parameters. In other embodiments, the calibration terms comprise functions to account for possible non-linear frequency responses of the sensors. Some non-diagonal elements of the calibration terms in the matrix of equation (5) may be zero, but in reality, it is more likely that each resonating sensor will have a cross-sensitivity to each of the environmental and chemical parameters. Although a matrix of calibration terms is presently preferred for convenience, it is not necessary to use a matrix to practice the invention. Instead, one could employ any system of equations in which each of the individual parameter values are determined using frequency responses from a plurality of sensors and corresponding calibration terms, to account for cross-sensitivity of each of the sensors to multiple environmental or chemical parameters. For example, one could use a system of equations similar to equations 6-11 without employing a matrix.

The sensor array 500 is preferably calibrated to determine the values of the calibration terms using transfer standard practices, where frequency responses of the sensors A-F are recorded for different known concentrations of target analytes at multiple, different points of environmental conditions (e.g., temperature, pressure, humidity, ambient light, etc.) in a range of potential operating conditions. The calibration data is stored either in a processor in the sensor array device or in a processor separate from the sensor array. In either case, the signals or data representative of the frequency responses of the sensors A-F may be de-convolved and analyzed to determine each individual parameter value that is substantially independent of the effects of variations in the other parameters.

Figure 12:
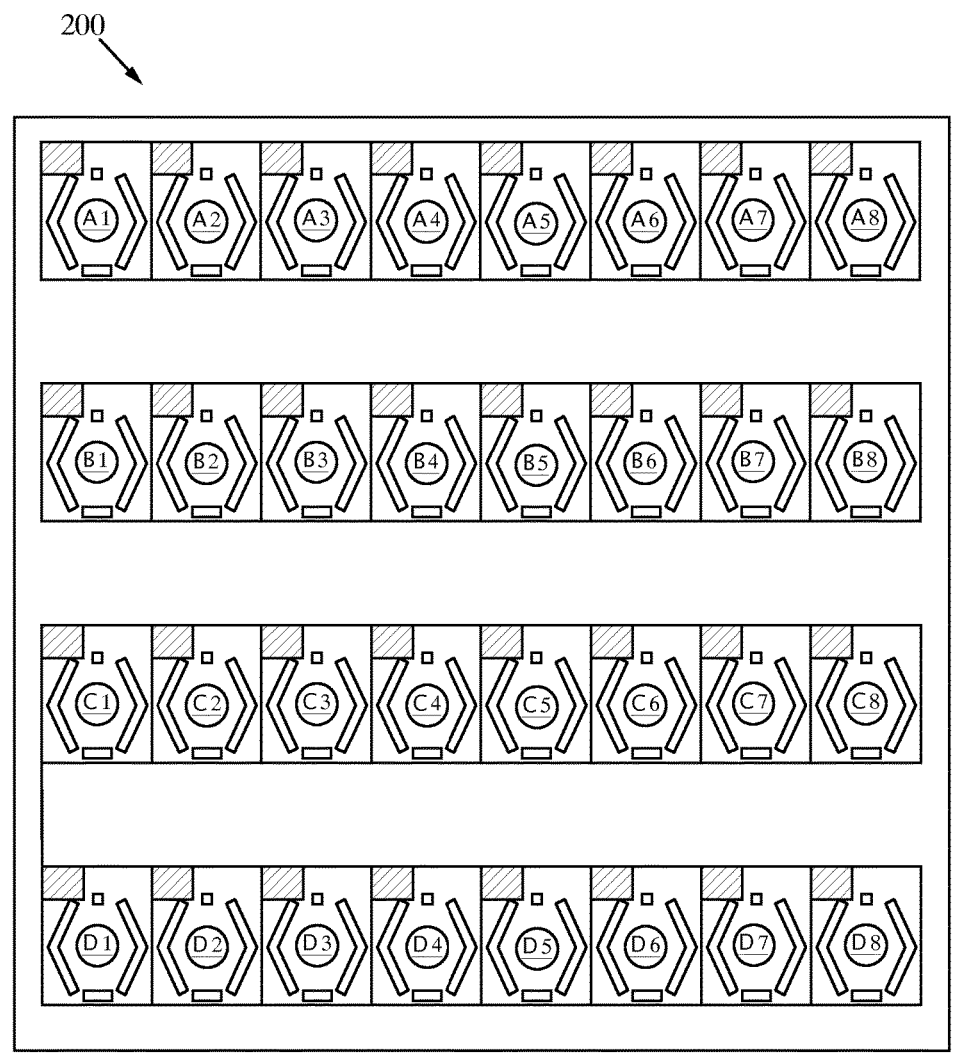
FIG. 12 shows a schematic, plan view of a sensor array according to another embodiment of the invention.

FIG. 12 is a schematic, plan view of a sensor array 200 according to another embodiment of the invention. The sensor array 200 comprises thirty-two sensors A1-D8. In some embodiments, thirty-two different individual parameter values are determined for environmental plus chemical parameters. In other embodiments, however, one may choose some redundancy to improve accuracy. For example, one may choose to employ thirty-two sensors A1-D8 to target a more limited set of eight total environmental plus chemical parameters.

The sensor array 200 may optionally include at least one reference sensor to provide a reference signal. The number of sensors in the array that will be used as reference may be easily determined experimentally. Typically, it is expected that 1% to 50% of the sensors in the array will be nonfunctionalized and used as a reference. In some embodiments, sensor arrays have a vast number of independently addressed sensors in the array to provide redundancy (e.g., an over-determined system). For instance, in an array of 5000 sensors, one can have a redundancy factor of 100 using 50 analyte and calibration sensors. This ensures that false alarms or defective elements in the arrays, which might miss the detection of analytes, are not an issue in device operation. The self-calibration and learning feature of such arrays is also a mode that takes full advantage of redundancy. It permits defective elements and the control quarantine and analytical potential of the device to be optimized on the fly. Furthermore, it permits new threatening chemicals that may be identified to be quickly introduced into the detection capabilities of machines installed at different operational locations.

Sensor arrays may be made with any of various known fabrication techniques including: silicon-on-insulator (SOI) bonding, sacrificial layer, and surface or bulk micromachining. The sensor is preferably designed for maximum sensitivity while taking into consideration its mechanical loading and electrical interfacing into the integrated (or non-integrated) electronic circuitry. Sensors may be integrated with electronics in any of various known configurations including: flip chip bonding, elements constructed on top of electronics, or vice versa. The sensors may be fabricated with through-wafer vias or trenches isolated by etching through the backside using various well-known techniques for cMUT fabrication. Techniques suitable for fabricating such sensors are known in the art and are described, for example, in B. T. Khuri-Yakub and L. Levin, U.S. Pat. No. 5,828,394, which is incorporated herein by reference.

In operation, a sensor array can be mounted on a wall, ceiling or other portion of a fixed structure, incorporated into a hand-held device, or mounted on a moving vehicle, to name just a few methods of exposing the sensor array to a sample. Depending on the specific application, it may be used with or without active circulation of analyte-containing gas or liquid over the sensors to increase exposure of the sensor to analytes (e.g., target molecules) in the environment. A general guideline for high sensitivity in detection of small quantities of materials is to position the sensor as close to the sampling inlet as possible. The small dimensions of the sensor arrays readily facilitate the integration of the sensor at even millimeter distances from a sampling inlet. Ring arrays may be made with sensor elements that are 30 microns (µm) in diameter and where nine sensor elements are connected together to form a sensor, thus making a sensor that 100 microns by 100 microns in size. Resonant devices may be made with sub-100 micron dimensions.

It will be clear to one skilled in the art that the above embodiments may be altered in many ways without departing from the scope of the invention. Many different permutations or arrangements may be used to realize the device and method of the invention. For example, sensor arrays containing multiple sensors may have membranes with different resonant frequencies. A membrane operating at low frequency yields a sensor more sensitive to stress on the membrane, whereas a membrane operating at high frequency gives a sensor that is more sensitive to mass loading. Combining various operating frequencies in one sensor thus provides a sensor with a greater versatility.

In some embodiments, electronics are integrated with sensor arrays, where multiple sensors are attached in parallel, and sensors are operated at different frequencies so that one output line may be used. For this purpose, different sensors may be built and operated at different frequencies. For example, a row of sensors can be made to resonate from 45 MHz to 55 MHz in 0.1 MHz intervals. Principles of dense wavelength division multiplexing (DWDM) may be used in such devices. A sensor for a Dog Nose type sensor may be made of one of multiple capacitor membranes that are all attached in parallel by virtue of having a metal electrode that covers all the sensors partially or fully. By altering the diameter of resonating members, it is possible to change the frequency of operation. Having sensors operating at multiple frequencies can have advantages in electronic integration in transmitting information at different frequencies on the same channel, and in separating the influence of stress and mass loading on the shift in resonant frequency of a resonator.

In some embodiments, arrays of sensors are functionalized by a wide range of receptor materials. For example, for polymer receptor materials, some 500 polymers with a redundancy factor of 10 may be used. The specific responses including orthogonality of response, operation mode (temperature, integration times, etc.), lifetime and sensitivity of environment or other disrupting influences may be tested using the target molecules and interfering agents. Based on a self-optimization the system may then select the most sensitive polymer basis set (say 10 polymers) and optimum mode of operation. In this way, different customers, corporate (food, perfume), medical (breath, urine, blood analysis), security or military can obtain rapidly prototyped solutions. Incorporation of this data in a database for future development of prototypes and known response functions can be used.

Accordingly, the scope of the invention should be determined by the following claims and their legal equivalents.

What is claimed is:

1. A device comprising:
    a) an array of resonant sensors having varied frequency responses to N environmental parameters and M chemical parameters, wherein N is an integer greater than or equal to 2, M is an integer greater than or equal to 1, and at least (N+M) of the sensors have different, non-zero frequency responses to at least two of the parameters;
    b) at least one detector for detecting frequency responses of the resonant sensors; and
    c) at least one processor in communication with the detector for receiving signals or data representative of the frequency responses, wherein the processor is programmed to determine individual parameter values for each of the chemical parameters according to the detected frequency responses and a system of equations using at least one matrix of calibration terms that relate the detected frequency responses to the individual parameter values, wherein each of the individual parameter values is calculated using the frequency responses of at least two of the resonant sensors, and the matrix has at least (N+M) rows, at least (N+M) columns, and off-diagonal elements with non-zero values.

2. The device of claim 1, wherein at least one of the resonant sensors has a resonating member coated with at least one metal-organic framework.

3. The device of claim 1, wherein the calibration terms comprise functions.

4. The device of claim 1, wherein the processor is further programmed to determine individual parameter values for each of the N environmental parameters according to the detected frequency responses and the equations, and each of the individual parameter values of the N environmental parameters is calculated using the frequency responses of at least two of the resonant sensors.

5. A device comprising:
a) an array of resonant sensors having varied frequency responses to N environmental parameters and M chemical parameters, wherein N is an integer greater than or equal to 2, M is an integer greater than or equal to 1, at least (N+M) of the sensors have different, non-zero frequency responses to at least two of the parameters, and at least one of the sensors has a resonating member coated with a metal film that reflects light;
b) at least one detector for detecting frequency responses of the resonant sensors; and
c) at least one processor in communication with the detector for receiving signals or data representative of the frequency responses, wherein the processor is programmed to determine individual parameter values for each of the M chemical parameters according to the detected frequency responses and a system of equations using calibration terms that relate the detected frequency responses to the individual parameter values, and each of the individual parameter values is calculated using the frequency responses of at least two of the resonant sensors.

6. The device of claim 5, wherein at least one of the resonant sensors has a resonating member coated with at least one metal-organic framework.

7. A device comprising:
a) an array of resonant sensors having varied frequency responses to N environmental parameters and M chemical parameters, wherein N is an integer greater than or equal to 2, M is an integer greater than or equal to 1, at least (N+M) of the resonant sensors have different, non-zero frequency responses to at least two of the parameters, each of the resonant sensors has at least one resonating member, and the resonating member of at least one of the sensors has a hydrophobic coating relative to a hydrophilic coating on the resonating member of another one of the sensors;
b) at least one detector for detecting frequency responses of the resonant sensors; and
c) at least one processor in communication with the detector for receiving signals or data representative of the frequency responses, wherein the processor is programmed to determine individual parameter values for each of the M chemical parameters according to the detected frequency responses and a system of equations using calibration terms that relate the detected frequency responses to the individual parameter values, and each of the individual parameter values is calculated using the frequency responses of at least two of the resonant sensors.

8. The device of claim 7, wherein at least one of the resonant sensors has a resonating member that is coated with at least one metal-organic framework.

9. The device of claim 7, wherein the resonating member of at least one of the sensors in the array has a thickness that is at least twice the thickness of the resonating member of another one of the sensors in the array.

10. The device of claim 7, wherein at least one of the sensors has a resonating member with a hole or perforation.

11. The device of claim 7, wherein the processor is further programmed to determine individual parameter values for each of the N environmental parameters according to the detected frequency responses and the equations, and each of the individual parameter values of the N environmental parameters is calculated using the frequency responses of at least two of the resonant sensors.

12. A device comprising:
a) an array of resonant sensors having varied frequency responses to N environmental parameters and M chemical parameters, wherein N is an integer greater than or equal to 2, M is an integer greater than or equal to 1, at least (N+M) of the sensors have different, non-zero frequency responses to at least two of the parameters, and at least one of the sensors has a resonating member composed of at least two materials having different coefficients of thermal expansion;
b) at least one detector for detecting frequency responses of the resonant sensors; and
c) at least one processor in communication with the detector for receiving signals or data representative of the frequency responses, wherein the processor is programmed to determine individual parameter values for each of the M chemical parameters according to the detected frequency responses and a system of equations using calibration terms that relate the detected frequency responses to the individual parameter values, and each of the individual parameter values is calculated using the frequency responses of at least two of the resonant sensors.

13. The device of claim 12, wherein at least one of the resonant sensors in the array has a resonating member coated with at least one metal-organic framework.

14. A method comprising:
a) exposing a sensor array to a sample, wherein the sensor array comprises a plurality of resonant sensors having varied frequency responses to N environmental parameters and M chemical parameters, N is an integer greater than or equal to 2, M is an integer greater than or equal to 1, and at least (N+M) of the sensors have different, non-zero frequency responses to at least two of the parameters;
b) detecting frequency responses of the sensors; and
c) employing at least one processor to determine individual parameter values for each of the M chemical parameters according to the detected frequency responses and a system of equations using at least one matrix of calibration terms that relate the detected frequency responses to the individual parameter values, wherein each of the individual parameter values is calculated using the frequency responses of at least two of the resonant sensors, and the matrix has at least (N+M) rows, at least (N+M) columns, and off-diagonal elements with non-zero values.

15. The method of claim 14, wherein at least one of the resonant sensors has a resonating member that is coated with at least one metal-organic framework.

16. The method of claim 14, wherein the calibration terms comprise functions.

17. The method of claim 14, further comprising the step of employing the processor to determine individual parameter values for each of the N environmental parameters according to the detected frequency responses and the calibration terms in the matrix, wherein each of the individual parameter values of the N environmental parameters is calculated using the frequency responses of at least two of the resonant sensors.

18. A method comprising:
a) exposing a sensor array to a sample, wherein the sensor array comprises a plurality of resonant sensors having varied frequency responses to N environmental parameters and M chemical parameters, N is an integer greater than or equal to 2, M is an integer greater than or equal to 1, at least (N+M) of the sensors have different, non-zero frequency responses to at least two of the parameters, and at least one of the sensors has a resonating member coated with a metal film that reflects light;

b) detecting frequency responses of the sensors; and c) employing at least one processor to determine individual parameter values for each of the M chemical parameters according to the detected frequency responses and a system of equations using calibration terms that relate the detected frequency responses to the individual parameter values, wherein each of the individual parameter values is calculated using the frequency responses of at least two of the resonant sensors and the corresponding calibration terms.

19. The method of claim 18, wherein at least one of the resonant sensors has a resonating member that is coated with at least one metal-organic framework.

20. A method comprising:

a) exposing a sensor array to a sample, wherein the sensor array comprises a plurality of resonant sensors having varied frequency responses to N environmental parameters and M chemical parameters, N is an integer greater than or equal to 2, M is an integer greater than or equal to 1, at least (N+M) of the sensors have different, non-zero frequency responses to at least two of the parameters, each of the sensors comprises at least one resonating member, and the resonating member of at least one of the sensors has a hydrophobic coating relative to a hydrophilic coating on the resonating member of another one of the sensors in the array;

b) detecting frequency responses of the sensors; and c) employing at least one processor to determine individual parameter values for each of the M chemical parameters according to the detected frequency responses and a system of equations using calibration terms that relate the detected frequency responses to the individual parameter values, wherein each of the individual parameter values is calculated using the frequency responses of at least two of the resonant sensors and the corresponding calibration terms.

21. The method of claim 20, wherein at least one of the resonant sensors has a resonating member that is coated with at least one metal-organic framework.

22. The method of claim 20, wherein the processor is further programmed to determine individual parameter values for each of the N environmental parameters according to the detected frequency responses and the equations, and each of the individual parameter values of the N environmental parameters is calculated using the frequency responses of at least two of the resonant sensors and the corresponding calibration terms.

23. A method comprising:

a) exposing a sensor array to a sample, wherein the sensor array comprises a plurality of resonant sensors having varied frequency responses to N environmental parameters and M chemical parameters, N is an integer greater than or equal to 2, M is an integer greater than or equal to 1, at least (N+M) of the sensors have different, non-zero frequency responses to at least two of the parameters, and at least one of the sensors comprises a resonating member composed of at least two materials having different coefficients of thermal expansion;

b) detecting frequency responses of the sensors; and c) employing at least one processor to determine individual parameter values for each of the M chemical parameters according to the detected frequency responses and a system of equations using calibration terms that relate the detected frequency responses to the individual parameter values, wherein each of the individual parameter values is calculated using the frequency responses of at least two of the resonant sensors and the corresponding calibration terms.

24. The method of claim 23, wherein at least one of the resonant sensors has a resonating member that is coated with at least one metal-organic framework.

\* \* \* \* \*